United States Patent
Fox et al.

(10) Patent No.: US 6,241,971 B1
(45) Date of Patent: Jun. 5, 2001

(54) HAIR STYLING COMPOSITIONS COMPRISING MINERAL SALT, LIPOPHILIC MATERIAL, AND LOW LEVELS OF SURFACTANT

(75) Inventors: Mary Mora Fox, Maineville, OH (US); Dana Hance Wolsing, Morning View, KY (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 08/937,637

(22) Filed: Sep. 25, 1997

(51) Int. Cl.⁷ ............................ A61K 7/00; A61K 7/08
(52) U.S. Cl. .................. 424/47; 424/70.19; 424/70.9; 424/70.21; 424/70.22; 424/70.23; 424/70.24; 424/70.27; 424/70.28; 424/70.31; 514/944; 514/945
(58) Field of Search ................... 424/70.1, 70.19, 424/70.9, 70.21, 70.22, 70.23, 70.24, 70.27, 70.28, 70.32; 514/944, 945

(56) References Cited

U.S. PATENT DOCUMENTS

| | | |
|---|---|---|
| 4,472,297 | 9/1984 | Bolich, Jr. et al. . |
| 4,606,913 | 8/1986 | Aronson et al. . |
| 5,030,443 | 7/1991 | Varco et al. . |
| 5,100,658 | 3/1992 | Bolich, Jr. et al. . |
| 5,124,078 * | 6/1992 | Baust .................. 252/546 |
| 5,149,522 * | 9/1992 | Schwarz ................ 424/70 |
| 5,326,483 * | 7/1994 | Halloran .............. 252/174.15 |
| 5,472,697 | 12/1995 | Hirano et al. . |
| 5,556,628 | 9/1996 | Derian et al. . |
| 5,587,170 | 12/1996 | Caisey et al. . |

FOREIGN PATENT DOCUMENTS

| | | |
|---|---|---|
| 2608649 | 9/1977 | (DE) . |
| 2810812 | 9/1979 | (DE) . |
| 9210516 | 12/1993 | (DE) . |
| 920516 U | 1/1994 | (DE) ................. A61K/7/08 |
| 0399157 | 11/1990 | (EP) . |
| 629395 | 12/1994 | (EP) . |
| 06425710 | 1/1989 | (JP) . |
| 01190620 | 7/1989 | (JP) . |
| 04217609 | 8/1992 | (JP) . |
| 05025022 | 2/1993 | (JP) . |
| 06172139 | 6/1994 | (JP) . |
| 07010720 | 1/1995 | (JP) . |
| 08403437A1 * | 9/1984 | (WO) . |
| 94/00099 | 1/1994 | (WO) . |
| 96/12787 | 5/1996 | (WO) . |
| 96/19182 | 6/1996 | (WO) . |
| 96/32921 | 10/1996 | (WO) . |

* cited by examiner

*Primary Examiner*—Thurman K. Page
*Assistant Examiner*—Brian K. Seidleck
(74) *Attorney, Agent, or Firm*—Stephen T. Murphy; Armina E. Matthews; Fumiko Tsuneki

(57) ABSTRACT

The present invention relates to leave-on hair styling compositions comprising from greater than 0.5% to about 5% of a water soluble, non-polymeric mineral salt, from about 0.05% to about 0.5% of a lipophilic material, from about 0.01% to about 0.5% of a surfactant, and an aqueous carrier. The surfactant is selected from the group consisting of amphoteric surfactants, anionic surfactants, and nonionic surfactants having the formula $$RX(OCH_2CH)_nOH,$$
$$|$$
$$Y$$

or $R_1R_2R_3Z \rightarrow O$, and mixtures thereof. The compositions comprise less than 0.01% cationic surfactant, less than about 0.2% of a chemical protein modifying agent, less than 0.01% formate, sorbate, salicylate and carbonate compounds, and less than about 0.2% of a polymer having a solubility parameter of from about 8.5 to about 12.0 $(cal/cm^3)^{1/2}$. Further, the composition has a hair friction index of at least 1.07.

19 Claims, No Drawings

HAIR STYLING COMPOSITIONS COMPRISING MINERAL SALT, LIPOPHILIC MATERIAL, AND LOW LEVELS OF SURFACTANT

TECHNICAL FIELD

The present invention relates to hair styling compositions comprising water soluble, non-polymeric mineral salts and lipophilic materials which provide improved hair styling. Specifically, the present invention relates to hair styling compositions comprising water soluble, non-polymeric mineral salts and lipophilic materials further comprising low levels of a dispersing surfactant for improved hair styling.

BACKGROUND OF THE INVENTION

Hair styling compositions, such as hair sprays, styling gels, spray-on gels, and mousses are used on hair to hold the hair in a particularly desired shape or arrangement. A hair arrangement having improved lift, volume and fullness is often a desirable attribute, particularly among consumers with fine, limp or less voluminous hair. Conventional volumizing products generally provide such lift, fullness, control and styling by using fixative resins and polymers. However, these products can be perceived as imparting to hair a stiff, tacky, sticky type of texture, leaving the hair feeling overly coated and rough to the touch.

Chemical processing such as perming, bleaching, highlighting, coloring, and straightening is also a means whereby fullness and volume can be imparted to hair. However, styles typically controlled using such methods are not easily changeable and are frequently time consuming and labor intensive. Moreover, the chemicals employed in such methods can be caustic and somewhat damaging to hair when used excessively.

Mineral salts have been known to be useful as a means of increasing the viscosity of formulations and emulsions when combined with surfactants as disclosed in *Encyclopedia of Shampoo Ingredients* (A. L. L. Hunting, Micelle Press, 1983). *Encyclopedia of Conditioning Rinse Ingredients* (A. L. L. Hunting, Micelle Press, 1987).

Compositions containing water soluble, non-polymeric mineral salts have also been described as styling aids. For example, German Patent, DE 2,608,649 to Schulz discloses fat (oil) free compositions which incorporate water soluble, non-polymeric mineral salts to provide a lighter, looser setting of the hair. Schulz, however, fails to address compatibility issues which arise upon incorporating conventional oil or oil-like substances such as preservatives, perfume oils, vitamins, botanical extracts, fatty alcohols and the like. Such lipophilic substances have limited solubility in water. And, as such, tend to aggregate or "clump" in aqueous environments, resulting in decreased styling efficacy.

Therefore, a need exists for improved hair styling compositions containing water soluble, non-polymeric mineral salts which also provide for the uniform distribution or dispersion of aesthetic and/or antimicrobial, lipophilic materials. The present inventors have discovered that the use of low levels of surfactants in mineral salt solutions provide for the even and uniform dispersion of added lipophilic materials resulting in improved hair styling benefits.

It is therefore an object of the present invention to provide compositions having improved styling benefits of fullness and volume without leaving the hair sticky, stiff or coarse.

It is also an object of the present invention to provide improved hair styling compositions comprising a water soluble, non-polymeric mineral salt, lipophilic materials and low levels of surfactant to uniformly disperse the lipophilic material.

It is also an object of the present invention to provide improved hair styling sprays, foams, mousses, lotions, gels and creams comprising a water soluble, non-polymeric mineral salt, lipophilic materials and low levels of surfactant to uniformly disperse the lipophilic material which provide cleaner feeling hair without stiffness or stickiness under a variety of humidity conditions.

It is further the object of the present invention to provide an improved method for styling hair.

These and other objects will become readily apparent from the detailed description which follows.

SUMMARY OF THE INVENTION

The compositions of the present invention relate to hair styling compositions, comprising:

a.) from greater than 0.5% to about 5% by weight of the composition of a friction enhancing agent which is a water soluble, non-polymeric mineral salt;

b.) from about 0.05% to about 0.5% of by weight of the composition of a lipophilic material;

c.) from about 0.01% to about 0.5% by weight of the composition of a surfactant selected from the group consisting of amphoteric, anionic, nonionic and mixtures thereof wherein the nonionic surfactant has a formula selected from the group consisting of:

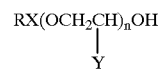

and mixtures thereof where R is a long chain alkyl group or mixer of alkyl groups containing 10–24 carbon atoms; X is a phenyl, $>C=O$, sulfur or nil; Y is a hydrogen or methyl; and n is an integer from 1 to 20, preferably from 2 to 15, and most preferably from 2 to 10; when X is nil, R is bonded directly to

and wherein $R_1$ contains an alkyl, alkenyl or monohydroxy alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group; and Z is a nitrogen, phosphorus or sulfur bonded directly to O;

and d.) water wherein the composition contains less than 0.01% cationic surfactant and wherein the composition contains less than about 0.2% by weight of the composition of a chemical protein modifying agent and wherein the composition contains less than 0.01% formate, sorbate, salicylate and carbonate and wherein the composition contains less than about 0.2% of a polymer having a solubility parameter of from about 8.5 to about 12.0 $(cal/cm^3)^{1/2}$ and wherein the composition has a hair friction index of at least 1.07.

The present invention further relates to methods of using the hair styling compositions.

DETAILED DESCRIPTION OF THE INVENTION

The hair styling compositions of the present invention can comprise, consist of, or consist essentially of the essential elements and limitations of the invention described herein, as well any of the additional or optional ingredients, components, or limitations described herein.

All percentages, parts and ratios are based upon the total weight of the personal cleansing compositions of the present invention, unless otherwise specified. All such weights as they pertain to listed ingredients are based on the active level and, therefore, do not include carriers or by-products that may be included in commercially available materials, unless otherwise specified.

The compositions of the present invention preferably contain less than 0.2% of an insoluble, inorganic salt complex. The term "insoluble inorganic salt complexes", as used herein, wherein the solubility of the inorganic salt complex is less than 0.5% in water at ambient temperature and pressure (25° C., 1 atmosphere pressure) includes but is not limited to, clays, bentonite, ceramic, kaolin, slip clays, polyorganosilicates, kaolinite, montmorillonite, atapulgite, illite, bentonite, halloysite, silica, alumina, mudds and polyphosphates.

The phrase "leave-on", as used herein, means compositions which are intended to be applied to hair, wet or dry and left on the hair during subsequent drying or styling. The compositions of the present invention are preferably leave-on compositions.

The compositions of the present invention contain less than about 0.2% of a chemical protein modifying agent, preferably less than about 0.15%, more preferably less than about 0.1%. The phrase "chemical protein modifying agent," as used herein means any chemical agent known to alter the chemical bond structure of the hair's protein in such a way as to lead to oxidative or reductive changes to bond links within the hair. Examples of, but not limited to, chemical protein modifying agents including ammonium thiglycolate, dithiothreitol, 1-3-dithiopropanol, glycerylmonothioglycolate, permanganate, peracetic acid, hydrogen peroxide, sodium thiosulfate, potassium sulfite, sodium bisulfite, sodium persulfate, and sodium hydroxide.

The phrase "stable dispersion," as used herein, means that the lipophilic materials are uniformly and homogenously distributed or dispersed within the compositions of the present invention without flocculating and phase separating when stored at 45° C. for at least a week, preferably for at least 1 month and most preferably for at least 3 months.

As used herein, the term "water soluble" refers to any material that is sufficiently soluble in water to form a substantially clear solution to the naked eye at a concentrations of 0.5% or more by weight of the material in the water at 25° C. Conversely, the term "water insoluble" refers to all materials that are not sufficiently soluble in water to form a substantially clear solution to the naked eye at a concentration of about 0.5% or more by weight of the insoluble material in water at 25° C.

The compositions of the present invention contain less than about 0.2% of a polymer having a solubility parameter of between about 8.5 to about 12.0 $(cal/cm^3)^{1/2}$. The solubility parameter is defined in the Polymer Handbook 3rd ed. (John Whiley and Sons, New York), J. Brandrup and E. H. Immergut, Chapter VII, pp. 519–559 as the square root of the cohesive energy density and describes the attractive strength between molecules of the material. Solubility parameters may determined by direct measurement, correlations with other physical properties, or indirect calculation. The solubility parameters of polymers can be determined by indirect calculations of group contributions as described in section 2.3 on p. 524–526 of the cited reference.

The hair styling compositions of the present invention, including the essential and optional components thereof, are described in detail hereinafter.

ESSENTIAL COMPONENTS

Water Soluble, Non-Polymeric Mineral Salt

An essential component of the hair styling compositions of the present invention is a friction enhancing agent which is a water soluble, non-polymeric mineral salt. By the term "non-polymeric", as used herein means the mineral salts of the present invention comprise no molecules comprising non-repeating moieties units (monomers). Without being limited by theory, it is believed that when the water soluble, non-polymeric mineral salt is solubilized and the resultant solution applied to (and dried on) the hair, the water soluble salt begins to precipitate onto the surface of the dry hair, increasing the hair's overall surface friction, thus improving styling volume and fullness. Suitable water soluble, non-polymeric mineral salts include naturally occurring or synthetically derived, anhydrous and hydrate forms of mono-, di- and trivalent inorganic salts as well as organic salts. Surfactant salts and salt polymers themselves are not included in the present electrolyte definition but other salts are. Suitable anionic salt substituents include, but are not limited to, halides, carbonates, phosphates, sulfates, nitrates, citrates, malates, gluconates, lactates, maleates, succinates, acetates, benzoates, fumerates and the like. The counter ions of such anionic substituents are metal ions and can be, but are not limited to, magnesium, calcium, sodium, potassium, or other mono- and divalent cations. Electrolytes most preferred for use in the compositions of the present invention include sodium, potassium and magnesium sulfates; sodium and potassium hydrogen carbonates or hydrogen sulfates; sodium and potassium carbonates; sodium, potassium, magnesium and calcium primary phosphates as well as sodium and potassium secondary phosphates. It is recognized that these salts may serve as thickening aids or buffering aids in addition to their role in increasing hair friction. The water soluble, non-polymeric mineral salt is preferably present at concentration levels of greater than 0.5% to about 5%, more preferably from about 0.7% to about 4%, most preferably from about 1% to 3%.

Lipophilic Materials

Also useful to the compositions of the present invention are lipophilic materials. The phrase "lipophilic material" is defined as a material having a solubility of less than 0.5% in water, preferably less than about 0.3% and most preferably less than about 0.1%.

Oils useful in the present invention are both natural and synthetically produced oils comprising saturated and unsaturated fatty acids. Saturated fatty acids found in the hydrocarbon oils of the present invention are selected from the group consisting of adipic, caprylic, captic, lauric, myristic, palmitic, stearic, and mixtures thereof. Unsaturated fatty acids found in the oils of the present invention are selected from the group consisting of linoleic, linolenic, ricinoleic, oleic, elaidic, erucic, and mixtures thereof. The oils used herein typically are mixtures of the above fatty acids. Oils derived from natural sources such as plants contain mixtures of the above mentioned fatty acids and mono-, di- and triglycerides. These oils include castor bean oil, or castor oil, rapeseed oil, corn oil, canola oil, peanut oil, avocado oil, soybean oil, palm kernel oil, babassu kernel oil, coconut oil, and mixtures thereof. A more detailed discussion as well as further examples of suitable of fatty acid derivative oils and hydrocarbon oils is found in U.S. Pat. No. 5,593,662 (Deckner, et. al.), herein incorporated by reference in its entirety.

Examples of preferred lipophilic materials include, but are not limited to, perfume oils, preservatives, oil soluble pro-vitamins, and essential oils and mixtures thereof, most preferably preservatives and perfumes and mixtures thereof.

Non-limited examples of preservatives useful in the present invention are benzyl alcohol, and parabens such as methyl paraben, propyl paraben, butyl paraben, and Liqua-Par oil (mixture of isobutyl paraben, isopropyl paraben, and butyl paraben).

As used herein, the term "perfume oil" means any odoriferous material or any material which acts as a malodor counteractant. In general, such perfume oils are characterized by a vapor pressure greater than atmospheric pressure at ambient temperatures. The perfume suitable for use in the present invention will be liquid oils at ambient temperatures. A wide variety of chemicals are known for perfumery uses, including materials such as aldehydes, ketones, esters and the like. More commonly, naturally occurring plant and animal oils and exudates comprising complex mixtures of various chemical components are known for use as perfumes, and such materials can be used herein. Perfumes suitable for use in the compositions of the present invention are described U.S. Pat. No. 5,676,584 (Angell et. al.) and further disclosed in S. Arctander, Perfume Flavors and Chemicals, Vols. I and II, Author, Montclair, N.J., and the Merck Index, 12th Edition, Merck & Co., Inc. Rahway, N.J., all of which are herein incorporated by reference in their entirety.

Non limiting examples of oil-soluble vitamins and vitamins A, vitamins D, vitamins E, vitamins K, and ubiquinones are found in U.S. Pat. No. 5,489,303 (Saski et. al.), herein incorporated by reference in its entirety.

The lipophilic materials of the present invention also include essential oils. Examples of suitable essential oils are found in U.S. Pat. No. 5,665,689 (Durbut), herein incorporated by reference in its entirety.

Mixtures of the above lipophilic materials may also be used. The lipophilic materials of the present invention are preferably present at concentration levels of from about 0.05% to about 0.5%, preferably from about 0.05% to about 0.3%, most preferably from about 0.05% to about 0.2%.

Surfactant

The hair styling compositions of the present invention also require a surfactant. Preferably the surfactants of the present invention are water soluble surfactants. By "water-soluble surfactant" is meant surfactant materials which form clear solutions when dissolved in water at 0.2 weight percent at ambient conditions. For the purposes of the present invention, the term "clear" is intended to mean that the solution formed is substantially transparent to visible light although a slight amount of haze may be present as long as one can see through the composition. Surfactants suitable for use in the present compositions include anionic surfactants, amphoteric surfactants and mixtures thereof as well as nonionic surfactants, cationic surfactants or mixtures thereof. Amphoteric surfactants useful in the present composition include those known to be useful in cosmetic compositions, and which, preferably, contain a group that is anionic at the pH of the compositions of the present invention.

Examples of amphoteric surfactants suitable for use in the compositions are described in U.S. Pat. No. 4,472,297 (Bolich Jr. et. al.); U.S. Pat. No. 5,104,646 (Bolich Jr. et. al.); and U.S. Pat. No. 5,106,609 (Bolich Jr. et. al.) and can be further described in "Surfactant Science Series: Amphoteric Surfactants", Volume 12, edited by Bernard R. Bluestin, Clifford L. Hilton, Marcel Dekker, New York (1982) all of which are herein incorporated by reference in their entirety. Mixtures of the above described amphoteric surfactants can be used. Preferred amphoteric surfactants for use in the compositions of the present invention include sodium lauroamphoacetate, and ammonium cocoyl isethionate.

Another preferred class of amphoterics, sometimes classified as zwitterionics, are betaines. Examples of betaines useful herein include the high alkyl betaines, such as cocoamidopropyl betaine. Mixtures of any of the amphoteric surfactants can be used in the composition of the present invention.

Also suitable for use in the present invention are anionic surfactants. Suitable anionic surfactants are described in U.S. Pat. No. 4,472,297 (previously incorporated by reference) and further described in "Surfactant Science Series: Anionic Surfactants", Volume 7, edited by Warner M. Linfield, Marcel Dekker, New York (1976), herein incorporated by reference in its entirety. Examples of suitable anionic surfactants include, but are not limited to, sodium lauryl sarcosinate, sodium lauryl sulfate, ammonium lauryl sulfate, sodium laureth sulfate, ammonium laureth sulfate, and disodium lauryl sulfosuccinate and mixtures thereof.

A preferred class of anionic surfactants includes alkyl glyceryl ether sulfonate surfactants (also referred to herein as an "AGS" surfactant), derivatives thereof and salts thereof. These AGS surfactants are derived from an alkyl glyceryl ether containing a sulfonate or sulfonate salt group. These compounds generally can be described as an alkyl monoether of glycerol that also contains a sulfonate group.

These AGS surfactants can be described as generally conforming to the following structures:

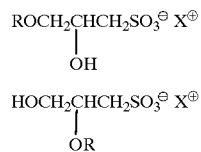

wherein R is a saturated or unsaturated straight chain, branched chain, or cyclic alkyl group having from about 10 to about 18 carbon atoms, preferably from about 11 to about 16 carbon atoms, and most preferably from about 12 to about 14 carbon atoms, and X is a cation selected from the group consisting of ammonium; mono-alkylsubstituted ammonium; di-alkylsubstituted ammonium; tri-alkylsubstituted ammonium; tetra-alkylsubstituted ammonium; alkali metal; alkaline metal; and mixtures thereof. More preferably, the alkyl radicals, R in the above formulas, are saturated and straight chain.

The AGS surfactants useful in the present invention are more fully described in U.S. Pat. No. 2,979,465, to Parran et. al., issued Apr. 11, 1961; U.S. Pat. No. 3,179,599, to Eaton et. al., issued Apr. 20, 1965; British Patent No. 848,224, published Sep. 14, 1960; British Patent No. 791,415, published Mar. 5, 1958; U.S. Pat. No. 5,322,643, to Schwartz et. al., issued Jun. 21, 1994; and U.S. Pat. No. 5,084,212, to Farris et. al. issued Jan. 28, 1992; which are all hereby incorporated herein by reference in their entirety. These references also disclose various cleansing products in which the AGS surfactant of this invention can be used. Mixtures of any of the above described anionic surfactants can be used in the composition of the present invention.

The surfactant component of the present invention may also include nonionic surfactants. Nonionic surfactants suitable for use in the compositions of the present invention have a formula selected from the group consisting of:

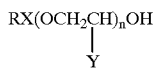

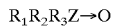

and mixtures thereof where R is a long chain alkyl group or mixer of alkyl groups containing 10–24 carbon atoms; X is a phenyl,

sulfur or nil; Y is a hydrogen or methyl; and n is an integer from 1 to 20, preferably from 2 to 15, and most preferably from 2 to 10; when X is nil, R is bonded directly to

and wherein $R_1$ contains an alkyl, alkenyl or monohydroxy alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxymethyl, hydroxyethyl, or hydroxypropyl radicals; where Z is a nitrogen, phosphorus or sulfur bonded directly to O (oxygen). The arrow in the formula is a conventional representation of a semipolar bond.

Nonionic surfactants suitable for use in the present compositions are described in U.S. Pat. No. 4,472,297 (previously incorporated by reference) and are further described in "Surfactant Science Series: Nonionic Surfactants", Volume 1, edited by Martin J. Schick, Marcel Dekker, New York (1966) all of which are herein incorporated by reference in its entirety. Mixtures of any of the above described nonionic surfactants can be used in the composition of the present invention.

Preferred for use in the compositions of the present invention are polyoxyalkylene alcohol surfactants, especially alkyl polyethyleneglycol ethers, alkyl polypropyleneglycol ethers, alkyl polyethylene glycol esters, and alkyl polypropylene glycol esters and mixtures thereof. Nonlimiting examples of suitable nonionic surfactants for use herein include Laureth-4, Ceteareth-10, Lauramine oxide, Dihydroxyethyl lauramine oxide and mixtures thereof.

Mixtures of any of the above-mentioned surfactants may be used herein. Without being limited by theory, it believed that the surfactant component of the present invention enables the even, stable and uniform dispersion of lipophilic materials which are poorly soluble in aqueous mixtures. The surfactant component of the present invention is preferably present at a concentration of from about 0.01 to about 0.5%, more preferably from about 0.02 to about 0.3%, most preferably from about 0.05 to about 0.2%. Additionally, the surfactant(s) of the present invention are preferably present in a ratio of mineral salt to surfactant of from about 2:1 to about 50:1, more preferably from about 2:1 to about 20:1, most preferably from about 5:1 to about 15:1.

Aqueous Hair Care Carrier

The compositions of the present invention also comprise a suitable aqueous hair care carrier. The aqueous hair care carrier herein can include water and other hydrophilic fluids, and combinations thereof. Suitable aqueous hair care carriers for use in the present invention, in addition to water, can include lower alcohols (C1–C4 alcohols). Preferred solvents include water, ethanol, and mixtures thereof. Especially preferred is water. The hair styling compositions of the present invention comprise from about 50% to about 99%, preferably from about 60% to about 99%, more preferably from about 75% to about 99%, by weight of aqueous hair care carrier.

OPTIONAL COMPONENTS

Compression Forms

The form in which the composition is delivered or applied will depend on the particular physical form and mode of delivery that the formulation is to achieve. Examples of suitable composition forms include tonics, gels, foams, mousses, creams, lotions, sprays and the like. Typical modes of delivery include application using the fingers; spraying (including mist, aerosol or foam spraying); and the like.

Additional Friction Enhancing Agent

The hair styling compositions of the present invention preferably contain relatively small amounts of conventional friction enhancing agents. The term "Friction enhancing agents", as used herein means agents which tend to raise the hair friction significantly versus water treated hair, as measured by the KES-SE Friction Test Method described below. Examples of such friction enhancing agents, other than the water soluble, non-polymeric minerals described above, include, but are not limited to natural and synthetic polymers and resins such as polyvinylpyrrolidone/vinyl acetate, polyquaternium-11, polyquaternium-4, butyl ester of polyvinylmethacrylate/methacrylate copolymer; inorganic clays such as bentonite, ceramic, kaolin, slip clays, polyorganosilicates, kaolinite, montmorillonite, atapulgite, illite, bentonite, halloysite, silica, alumina, mudds; water insoluble minerals such as calcium carbonate, calcium oxalate, calcium polyphosphates; sawdust; plant polysaccharides; and crustacean shells. Preferably, the additional friction enhancing agents are present at concentration levels of less than about 2%, more preferably about 1.5%.

Hair Friction Index Measurement Test

The hair styling compositions of the present invention preferably have a hair friction index of at least about 1.07, preferably 1.10, most preferably 1.15, as measured by the KES-SE Friction Test.

The KES-SE Friction Test Method evaluates the friction force of the surface of a flat hair switch. This is achieved with the use of a Friction instrument, KES-SE Model (by Kato Tech Ltd., Kyoto, Japan). Specific instructions for calibration, instrument operation and instrument care are provided by the manufacturer and are generally known to those of ordinary skill in the art. The hair friction index is determined as follows.

A round glass frit 25 mm in diameter, with a porosity =C is attached to the sensor probe. The probe with the frit is weighed to the nearest 0.01 grams. The weight of the probe with glass frit should be approximately 22 grams. A control group is prepared comprised of four hair switches made up of 8 grams of hair. Each hair switch is then water treated.

Water treatment of the control group switches comprises pre-wetting, shampooing and rinsing each hair switch using running water flowing at a flow rate of 1.5 cubic feet per min. Warm water ($\cong 40°$ C.) is used throughout the treatment process. The hair switches are blotted with a water-absorbing, nonwoven paper material. Approximately 0.1 grams of water per gram of hair switch is then applied uniformly to each hair switch and massaged throughout the hair. The hair switches are dried using a hot air ($\cong 55°$ C.) blower and combed to remove tangles for approximately 4 minutes. After the treated switches are dried, the switches are equilibrated to a constant moisture content in a constant temperature environment of 21° C. and having a constant humidity of 40% RH for no less than 2 hours and no longer than 4 hours. The probe is pulled longitudinally along the length of each water treated hair switch from the root end of the hair switch to the tip end of the switch. The probe (and frit) should be cleaned and dried before each measurement using an alcoholic or other non-residue forming solvent and zero calibrated to test the integrity of the system. Voltage readouts from the potentiometer of the KES-SE instrument are recorded at pre-set intervals (by the manufacturer) for each of the hair switches. The voltage readings are then converted to friction values using Equation 1.1:

$$\text{Friction} = [\text{voltage} \times 5]/[\text{weight of probe (g)}] \quad \text{Equation 1.1}$$

The friction value is determined for each of the hair switches of the control group.

Next, friction data is collected for the test group. The test group is comprised of four hair switches are pre-wetted, shampooed and rinsed as described above. Approximately 0.1 grams of the test product per gram of hair switch is then applied uniformly to each hair switch and massaged throughout the hair. The hair switches are dried using a hot air ($\cong 55°$ C.) blower and combed to remove tangles for approximately 4 minutes and then equilibrated to a constant moisture content in a constant temperature environment of 21° C. and having a constant humidity of 40% RH for no less than 2 hours and no longer than 4 hours. The friction values for each of the test group switches are then determined using the friction measurement procedure described above and Equation 1.1.

The Friction Index is determined by comparing the average friction reading of the 4 switches in the control group with the average reading of 4 switches of the test group using Equation 1.2.

$$\text{Friction Index} = \text{Friction}_{ave}(\text{test group})/\text{Friction}_{ave}(\text{control group}) \quad \text{Equation 1.2.}$$

Statistical significance is determined at the 90% confidence level ($p \leq 0.10$) by comparing the mean and variance of the 4 hair switches in the test group with the mean and variance of the 4 hair switches in the control group using the Two-sampled T-test. A more detailed discussion of the disclosed friction test method is found in "Methods for the Measurement of the Mechanical Properties of Tissue Paper", R. S. Ampuski, Int. Paper Phys. Conf., pp. 19–30 (1991).

Thickening Agent

The personal care compositions of the present invention may also comprise a thickener or thickening agent. Such thickening agents typically comprise cationic, nonionic, anionic, and amphoteric polymers. The thickening agent is preferably present at a level of less than about 2%, more preferably from about 0.05% to about 1.5% by weight of the composition.

Polymers suitable for use as thickening agents herein include any polymer soluble or colloidally dispersible in the aqueous phase (if water is the only solvent in the aqueous phase, the polymer should be soluble or dispersible in water; if an optional cosolvent such as ethanol is present the polymer should be soluble or dispersible in the combined solvent system). Solubility/dispersibility is determined at ambient conditions of temperature and pressure (25° C. at 1 At). Polymers for use in the compositions of the present invention include cationic, anionic, nonionic, and amphoteric resins. Polymeric thickeners useful in the present are described in U.S. Pat. No. 5,100,658 (Bolich, Jr. et. al.), herein incorporated by reference.

Nonlimiting examples of preferred thickening polymers include Polyquaternium-10 (hydroxyethylcellulose hydroxypropyl trimethylammonium chloride ether) under the trade name Ucare LR Polymers and JR Polymers, natural and derivatized polysaccharides which include guar gums, modified guar gums, locust bean gums, carrageenans, alginates, xanthan gums, sodium alginates, sodium carrageenans, plant extracts of acacia, ghatti, and tragacanth, propylene glycol alginate, and carboxymethylcellulose and mixtures thereof.

Pharmaceutical Actives

The compositions of the present invention, especially the topical skin care compositions, can comprise a safe and effective amount of a pharmaceutical active. The phrase "safe and effective amount", as used herein, means an amount of an active high enough to significantly or positively modify the condition to be treated, but low enough to avoid serious side effects (at a reasonable benefit/risk ratio), within the scope of sound medical judgment. A safe and effective amount of the pharmaceutical active will vary with the specific active, the ability of the composition to penetrate the active through the skin, the amount of composition to be applied, the particular condition being treated, the age and physical condition of the patient being treated, the severity of the condition, the duration of the treatment, the nature of concurrent therapy, and like factors.

The pharmaceutical actives which can be used in the compositions of the present invention preferably comprise from about 0.1% to about 20% by weight of the compositions, more preferably from about 0.1% to about 10%, and most preferably from about 0.1% to about 5%. Mixtures of pharmaceutical actives may also be used.

Useful pharmaceutical actives include analgesic actives, antipruritic actives, anesthetic actives, antimicrobial actives, sunscreen actives, anti-dandruff actives and mixtures thereof.

Nonlimiting examples of pharmaceutical actives useful in the present invention can be found in U.S. Pat. No. 5,622,694 (Torgerson et. al.), herein incorporated by reference in its entirety.

Other Optional Components

The hair styling compositions of the present invention may further comprise one or more optional components known for use in shampoo, conditioning, styling and other personal cleansing compositions, provided that the optional components are physically and chemically compatible with the essential component described herein, or do not otherwise unduly impair product stability, aesthetics or performance. Concentrations of such optional components typically range from about 0.001% to about 5% by weight of the hair styling compositions or more preferably from about 0.01 to about 3% by weight of the hair styling compositions.

Optional components include water-soluble preservatives such as Glydant (DMDM Hydantoin or dimethylol dimethyl hydantoin), Dowicil® (1-cis-3-chloroallyl-3-5-7-triaza), Kathon CG, (mixture of methylchloro-isothiazolinone and methyl isothiazolinone), imidazolidinyl urea, sodium benzoate, phenoxyethanol, EDTA and its salts; anti static agents; cationic conditioning polymers such as polyquaternium-10; dyes; organic solvents or diluents; emollient oils (such as polyisobutylene, mineral oil, petrolatum and isocetyl stearyl stearate); pearlescent aids; foam boosters; pediculocides; pH adjusting agents; proteins; antioxidants; chelators and sequestrants; colorings, skin sensates; astringents; skin soothing agents; skin healing agents and the like; non limiting examples of these components include panthenol and derivatives (e.g. ethyl panthenol), pantothenic acid and its derivatives, phytantriol; menthyl lactate, witch hazel distillate, allantoin, bisabalol, dipotassium glycyrrhizinate and the like; suspending agents; other plant and botanical extracts; water-soluble vitamins; and viscosity adjusting agents. This list of optional components is not meant to be exclusive, and other optional components can be used.

METHOD OF MANUFACTURE

The hair styling compositions of the present invention, in general, can be made by simply mixing together all components using low shear mixing methods. In compositions which use thickening agents, it is advantageous to first solubilize the thickening agents in water before the addition of the other components and the water soluble salts of the compositions.

METHOD OF USE

The hair styling compositions of the present invention are used in a conventional manner for applying styling products to the hair. An effective amount of the composition for treating the hair is applied to the hair, that has preferably been wetted with water, and then leaving the composition on the hair to dry or aiding in the drying process with hot air blow drier devices or heated implements. Such effective amounts generally range from about 0.5 g to about 50 g, preferably from about 1 g to about 20 g. Application to the hair typically includes contacting the hair with the composition and working the composition throughout the hair or specifically where the effect is most desired.

This method for treating the hair comprises the steps of: a) wetting the hair with water, b) applying an effective amount of the hair styling composition to the hair, and c) allowing the composition to dry on hair as the hair dries or is dried with a hot air appliance.

EXAMPLES

The hair styling compositions illustrated in Examples 1–6 illustrate specific embodiments of the styling compositions of the present invention, but are not intended to be limiting thereof. Other modifications can be undertaken by the skilled artisan without departing from the spirit and scope of this invention. These exemplified embodiments of the hair styling compositions of the present invention provide improved hair styling and conditioning.

All exemplified compositions can be prepared by conventional formulation and mixing techniques. Component amounts are listed as weight percents and exclude minor materials such as diluents, filler, and so forth. The listed formulations, therefore, comprise the listed components and any minor materials associated with such components.

EXAMPLE 1

The following is an example of a hair lotion incorporating the compositions of the present invention. The compositions are formed by combining and mixing the ingredients of each column using conventional technology and then applying to hair from about from about 0.5 g to about 50 g.

| LOTION COMPOSITION | % w/w |
|---|---|
| Xanthan Gum | 1.0 |
| Benzyl Alcohol | 0.25 |
| Quaternium-15 (Dowicil 200, Dow Chemical, Midland, MI) | 0.135 |
| Sodium Benzoate | 0.25 |
| Cocamidopropyl betaine (Tegobetaine F-B, Goldschmidt, Hopewell, VA) | 0.075 |
| Magnesium Sulfate Heptahydrate | 3.08 |
| Perfume | 0.06 |
| Citric Acid | 0.1 |
| Water | q.s. to 100% |

EXAMPLE 2

The following is an example of a hair lotion incorporating the compositions of the present invention. The compositions are formed by combining and mixing the ingredients of each column using conventional technology and then applying to hair from about from about 0.5 g to about 50 g.

| LOTION COMPOSITION | % w/w |
|---|---|
| Xanthan Gum | 1.0 |
| Benzyl Alcohol | 0.5 |
| Quaternium-15 (Dowicil 200, Dow Chemical, Midland, MI) | 0.135 |
| Cocamidopropyl betaine (Tegobetaine F-B, Goldschmidt, Hopewell, VA) | 0.075 |
| Magnesium Sulfate Heptahydrate | 3.08 |
| Perfume | 0.06 |
| Citric Acid | 0.1 |
| Water | q.s. to 100% |

EXAMPLE 3

The following is an example of a hair lotion incorporating the compositions of the present invention. The compositions are formed by combining and mixing the ingredients of each column using conventional technology and then applying to hair from about from about 0.5 g to about 50 g.

| LOTION COMPOSITION | % w/w |
|---|---|
| Xanthan Gum | 1.0 |
| Quaternium-15 (Dowicil 200, Dow Chemical, Midland, MI) | 0.135 |
| Sodium Benzoate | 0.25 |
| Cocamidopropyl betaine (Tegobetaine F-B, Goldschmidt, Hopewell, VA) | 0.075 |
| Magnesium Sulfate Heptahydrate | 3.08 |
| Perfume | 0.06 |
| Citric Acid | 0.2 |
| Water | q.s. to 100% |

EXAMPLE 4

The following is an example of a hair spray incorporating the compositions of the present invention. The compositions are formed by combining and mixing the ingredients of each column using conventional technology and then applying to hair from about from about 0.5 g to about 50 g.

| SPRAY COMPOSITION | % w/w |
|---|---|
| Xanthan Gum | 0.1 |
| Magnesium Sulfate heptahydrate | 2.05 |
| Sodium Benzoate | 0.25 |
| DMDM Hydantoin (Glydant, Lonza Inc., Fairlawn, NJ) | 0.20 |
| Cocamidopropyl betaine (Tegobetaine F-B, Goldschmidt, Hopewell, VA) | 0.075 |
| Perfume | 0.05 |
| Citric Acid | 0.1 |
| Water | q.s. to 100% |

EXAMPLE 5

The following is an example of a hair spray incorporating the compositions of the present invention. The compositions are formed by combining and mixing the ingredients of each column using conventional technology and then applying to hair from about from about 0.5 g to about 50 g.

| SPRAY COMPOSITION | % w/w |
|---|---|
| Polyquaternium-10 (U-Care Polymer LR-400, Amerchol, Edison, NJ) | 0.1 |
| Sodium Sulfate | 1.0 |
| DMDM Hydantoin (Glydant, Lonza Inc., Fairlawn, NJ) | 0.20 |
| Tetrasodium EDTA | 0.13 |
| Sodium Lauroyl Sarcosinate (Hamposyl L-30, Hampshire Chem. Corp., Lexington, MA) | 0.025 |
| Cocamidopropyl betaine (Tegobetaine F-B, Goldschmidt, Hopewell, VA) | 0.05 |
| Perfume | 0.05 |
| Laureth-4 (Brij 30, ICI Surfactants, Wilmington, DE) | 0.004 |
| Citric Acid | 0.05 |
| Water | q.s. to 100% |

EXAMPLE 6

The following is an example of a foam incorporating the compositions of the present invention. The compositions are formed by combining and mixing the ingredients of each column using conventional technology and then applying to hair from about from about 0.5 g to about 50 g.

| FOAM COMPOSITION | % w/w |
|---|---|
| Polyquaternium-10 (U-Care Polymer LR-400, Amerchol, Edison, NJ) | 0.25 |
| Sodium Sulfate | 1.0 |
| Tetrasodium EDTA | 0.13 |
| DMDM Hydantoin (Glydant, Lonza Inc., Fairlawn, NJ) | 0.20 |
| Cocamidopropyl betaine (Tegobetaine F-B, Goldschmidt, Hopewell, VA) | 0.015 |
| Laureth-4 (Brij 30, ICI Surfactants, Wilmington, DE) | 0.004 |
| Sodium Lauroyl Sarcosinate (Hamposyl L-30, Hampshire Chem. Corp., Lexington, MA) | 0.07 |
| Perfume | 0.05 |
| Citric Acid | 0.1 |
| Water | q.s. to 100% |

What is claimed is:

1. A hair styling composition, comprising:

a.) from greater than 0.5% to about 5% by weight of the composition of a friction enhancing agent which is a water soluble, non-polymeric mineral salt;

b.) from about 0.05% to about 0.5% of by weight of the composition of a lipophilic material;

c.) from about 0.01% to about 0.5% by weight of the composition of a surfactant selected from the group consisting of amphoteric, anionic, nonionic and mixtures thereof wherein the nonionic surfactant has a formula selected from the group consisting of:

$$RX(OCH_2CH)_nOH$$
$$\phantom{RX(OCH_2CH)_n}|$$
$$\phantom{RX(OCH_2CH)_n}Y$$

$$R_1R_2R_3Z \rightarrow O$$

and mixtures thereof where R is a long chain alkyl group or mixer of alkyl groups containing 10–24 carbon atoms; X is a phenyl, $$\begin{array}{c}\diagdown\\C=O,\\\diagup\end{array}$$

sulfur or nil; Y is a hydrogen or methyl; and n is an integer from 1 to 20, preferably from 2 to 15, and most preferably from 2 to 10; when X is nil, R is bonded directly to $$-(OCH_2CH)_{\overline{n}}-$$
$$\phantom{-(OCH_2CH}|$$
$$\phantom{-(OCH_2C}Y$$

and wherein $R_1$ contains an alkyl, alkenyl or monohydroxy alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group; and Z is a nitrogen, phosphorus or sulfur bonded directly to O;

and d.) aqueous hair care carrier wherein the composition contains less than 0.01% cationic surfactant and wherein the composition contains less than about 0.2% by weight of the composition of a chemical protein modifying agent and wherein the composition contains less than 0.01% formate, sorbate, salicylate and carbonate and wherein the composition contains less than about 0.2% of a polymer having a solubility parameter of from about 8.5 to about 12.0 $(cal/cm^3)^{1/2}$ and wherein the composition has a hair friction index of at least 1.07.

2. A composition according to claim 1, wherein the water soluble, non-polymeric mineral salt is selected from the group consisting of sodium, potassium, calcium and magnesium salts of sulfate, chloride, gluconate, lactate, acetate, and citrate.

3. A composition according to claim 2, wherein the concentration of the water soluble, non-polymeric mineral salt is from about 0.7% to about 4.0%.

4. A composition according to claim 1, wherein the anionic surfactant is selected from the group consisting of sulfates, sulphonates, taurines, sarcosinates, and isethionates and mixtures thereof.

5. A composition according to claim 4, wherein the anionic surfactant is selected from the group consisting of sarcosinates, isethionates and mixtures thereof.

6. A composition according to claim 1, wherein the amphoteric surfactant is selected from the group consisting of alkylbetaines, alkylamphoacetates and aklyaminopropionates and mixtures thereof.

7. A composition according to claim 6, wherein the amphoteric surfactant is selected from the group consisting of alkylbetaines, alkylamphoacetates and mixtures thereof.

8. A composition according to claim 1, wherein the nonionic surfactant is selected from the group consisting of alkyl polyethyleneglycol ethers, alkyl polypropyleneglycol ethers, alkyl polyethylene glycol esters, and alkyl polypropylene glycol esters and mixtures thereof.

9. A composition according to claim 8, wherein the alkyl polyethyleneglycol ether is Laureth-4.

10. A composition according to claim 1, wherein the concentration of the surfactant is from about 0.02% to about 0.3%.

11. A composition according to claim 1, wherein the lipophilic material is selected from the group consisting of perfume oils, preservatives, oil-soluble vitamins, oil-soluble pro-vitamins, essential oils and mixtures thereof.

12. A composition according to claim 11, wherein the preservative is selected from the group consisting benzyl alcohol, methyl paraben, propyl paraben, butyl paraben, isobutyl paraben, isopropyl paraben, and mixtures thereof.

13. A composition according to claim 12, further comprising a water-soluble preservative selected from the group consisting of DMDM Hydantoin, 1-cis-3-chloroallyl-3-5-7-triaza, methylchloro-isothiazolinone, methyl isothiazolinone, imidazolidinyl urea, sodium benzoate, fatty alcohol quats, phenoxyethanol, EDTA and its salts, and mixtures thereof.

14. A composition according to claim 11, wherein the perfume oil is selected from the group consisting of galaxolide, para-tertiary bucinal, benzyl acetate, hexyl cinnamic aldehyde, phenyl ethyl alcohol, citronellol, geraniol, dihydro iso jasmonate and mixtures thereof.

15. A composition according to claim 1 in the form of a tonic, spray, foam, mousse, lotion, gel, or cream.

16. A composition according to claim 1, further comprising a pharmaceutical active.

17. A composition according to claim 16, wherein the pharmaceutical active is selected from the group consisting of analgesic actives, antipruritic actives, anesthetic actives, antimicrobial actives, sunscreen actives, anti-dandruff actives and mixtures thereof.

18. A composition according to claim 1, further comprising a thickening agent at a concentration of from about 0.05% to about 1.5%.

19. A method of styling hair by administering a safe and effective amount of the compositions according to claim 1.

* * * * *